United States Patent [19]

Steinbach et al.

[11] Patent Number: 4,969,873
[45] Date of Patent: Nov. 13, 1990

[54] DEVICE FOR DISPENSING ACTIVE SUBSTANCES TO A PATIENT

[75] Inventors: Bernd Steinbach, Cologne, Fed. Rep. of Germany; Leopold Schlögl, Pottenstein, Austria

[73] Assignee: Annemarie Schlogl Gesellschaft m.b.H. & Co., KG, Pottenstein, Austria

[21] Appl. No.: 370,328

[22] Filed: Jun. 22, 1989

[30] Foreign Application Priority Data

Jun. 23, 1988 [AT] Austria .................. 1631/88

[51] Int. Cl.⁵ .............................................. A61M 5/00
[52] U.S. Cl. ...................... 604/93; 604/145; 604/891.1; 128/DIG. 12
[58] Field of Search ............... 604/131, 132, 133, 140, 604/141, 145, 83, 85, 86, 93, 175, 891.1

[56] References Cited

U.S. PATENT DOCUMENTS

| 3,731,681 | 5/1973 | Blackshear et al. | 604/141 |
| 4,299,220 | 11/1981 | Dorman | 604/141 |
| 4,525,165 | 6/1985 | Fischell | 604/131 |
| 4,619,652 | 10/1986 | Eckenhoff et al. | 604/145 |
| 4,915,690 | 4/1990 | Cone et al. | 604/93 |

Primary Examiner—Stephen C. Pellegrino
Assistant Examiner—Corrine Maglione
Attorney, Agent, or Firm—Marshall, O'Toole, Gerstein, Murray & Bicknell

[57] ABSTRACT

Septum for implantable devices for dispensing active substances, for example medicaments, to the body of the patient. The septum is inserted as a cover of a medicament chamber into the associated opening by means of one or more clamping members, the septum (22; 36; 10) being formed annularly with part (32) of the apparatus wall disposed within the septum and connected fixedly to the remaining housing (31).

4 Claims, 2 Drawing Sheets

DEVICE FOR DISPENSING ACTIVE SUBSTANCES TO A PATIENT

The invention relates to a septum for implantable devices for dispensing active substances, for example medicaments, to the body of the patient. The septum is sealingly inserted as a cover of a medicament chamber in the associated opening via one or more clamping members.

In known constructions of this type hitherto, a circular septum is used which is held in the device at the edge by clamping members. The center region of the septum freely spans the opening of the medicament chamber so that the size of the septum is limited by the span width in so far as the septum is a very elastic rubber-like body which after each insertion of an injection needle must close sealingly again and, as a result, if the span width is too great, on piercing, the septum bears on the bottom of the chamber and this greatly restricts filling of the chamber. Due to the very small area available in known constructions for piercing by means of an injection needle, each piercing point is used very often by the injection needle so that hitherto known septa soon show a tendency to leak.

The invention is based on the problem of providing a septum of the type mentioned at the beginning in which a larger area is available for piercing without changing the free span width of the septum.

According to the invention this problem is solved in that the septum is made annular, the portion of the device wall disposed within the septum being fixedly connected to the remaining housing. This achieves the goal that a substantially greater area is available for piercing with the injection needle so that the septum is not subjected to as much stress by the insertions of the injection needle. Although with the construction according to the invention, the device for dispensing active substances is somewhat greater in diameter. This disadvantage is more than compensated for by the substantially greater durability of the septum.

In particularly advantageous manner, the septum according to the invention is suitable for implantable devices for dosed dispensing of a substance, for example a medicament. Such a device may have two chambers separated from each other by a flexible membrane, one of which chambers contains the substance to be dispensed, having a dispensing opening connected to a dispensing catheter and a replenishing opening, and the other chamber being filled with a propellant which expands isobarically with evaporation to dispense the substance to be liberated. In such a construction the septum according to the invention can serve to seal the chamber containing the substance to be dispensed. This also makes it possible to achieve that replenishment of the chamber a substantially greater number of times without the septum becoming leaky.

The septum according to the invention is also advantageous in an implantable device for dosed dispensing of a substance, for example medicament, in which the device comprises two chambers which are separated from each other by a flexible membrane and the one chamber of which, containing the substance to be dispensed, being provided with a dispensing opening connected to a dispensing catheter and a filling opening, the other chamber being filled with a propellant which expands isobarically with evaporation for dispensing the material to be liberated, and between the dispensing opening of the chamber and the dispensing cathether a means is provided for an additional introduction of medicaments or the like into the outlet catheter. In such a device the annular septum can serve to seal the chamber for the additional introduction of medicaments, the septum being arranged round the replenishment opening. This achieves, in addition to the increase in the surface area to be pierced by the injection needle, that the septum can be located more easily. This location of the annular chamber can moreover also be considerably facilitated by a template which is placed on the skin of the patient, the position of the template being governed substantially by the feelable edge of the implanted device. Finally, the replenishing of the filling opening can be provided centrally in the device and the annular septum arranged concentrically to the replenishing opening. As a result for locating the annular septum the template can also be placed on the implanted device in such a manner that the center of the template coincides with the central outwardly projecting replenishing opening. The template then has at a distance from the center corresponding to the radius of the annular chamber a through opening which indicates the position of the annular chamber. When the position of the template is defined by the feelable edge of the implantable device the replenishing opening must then be disposed exactly centrally in the device. For determining the location of the annular chamber the edge of the template could also be used if the diameter thereof corresponds to that of the annular chamber.

Such implantable devices for dosed dispensing of a substance are generally used for directly introducing insulin or other long-term medicaments into the body, said devices being refilled using an injection syringe via the replenishing openings which are sealed by a septum. Now, however, it is frequently necessary to add additional medicament to the continuous dosing of the medicament. For this purpose it is already known to provide an additional chamber which communicates directly with the outlet catheter and via which additional medicament can be injected directly into the outlet catheter. Said chamber in the known construction is provided at the outer periphery of the device and like the replenishing opening, sealed with a circular septum through which, by means of an injection needle, the additional injection of medicament is possible. This known construction has the disadvantage that the physician injecting the additional medicament must first look for this opening of the chamber, additionally sealed with a septum, and this is not very simple with an implanted device. In addition, the point for additional introduction of the medicament is pierced very often by the injection needle and as a consequence of this there can be leaks in the septum. All these aforementioned disadvantages are eliminated by the construction according to the invention described above.

In the drawings some examples of embodiments of the subject of the invention are illustrated.

Figure 1:
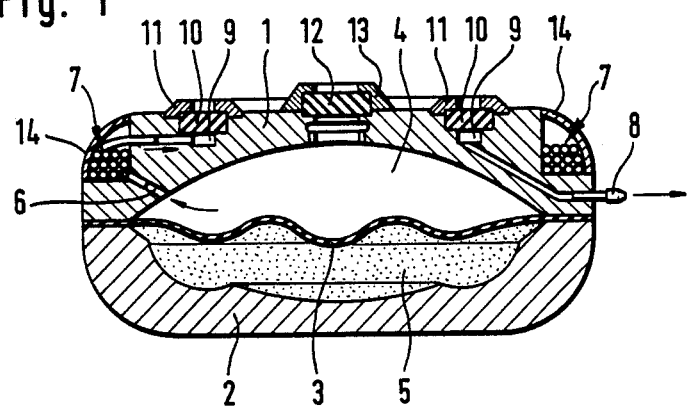
FIG. 1 shows a vertical section through a device provided with a septum according to the invention for dosed dispensing of a medicament, along the line I—I of FIG. 2.

The device comprises a housing which is made up of two parts 1, 2 and the interior of which is divided by a flexible membrane 3 into two chambers 4, 5. The chamber 4 is intended for receiving the medicament to be dispensed whilst the chamber 5 contains a propellant which under the body heat expands isobarically. By the expansion of the propellant the membrane 3 is influenced in the sense of displacing the medicament out of the chamber 4, the medicament being dispensed into the body of the patient via the outlet opening 6, an outlet reducing means 7 and an outlet catheter 8. Before the medicament reaches the outlet catheter 8 it is introduced into a chamber 9 which is provided annularly on the part 1 of the housing. Said chamber 9 is sealed at its upper side by a ring 10 which can be pierced by an injection needle and which automatically seals up again after withdrawal of the injection needle, i.e. by a septum. Said ring 10 is secured via an annular securing means 11 in its position. The chamber 4 can be replenished via a further septum 12 which is secured by means of a securing member 13.

In the present case the implantable device is constructed as a circular body, the replenishing opening 12 being arranged centrally in the device and the annular chamber 9 concentrically thereto. To locate the annular chamber 9 a template, not illustrated, can be placed onto the skin of the patient in such a manner that the center of the template coincides with the replenishing opening. At a distance from the center corresponding to the radius of the annular chamber the template comprises a hole which after corresponding placing of the template is located over the annular chamber so that when the injection needle is inserted through the hole the annular chamber is reliably found.

The outlet reducing means 7 in the present case is a tube winding, which in the present case is wound around several times in a recess of the part 1 of the housing. Said recess is sealed by a cover 14 in such a manner that a smooth outer contour of the implantable device is achieved.

Figure 2:
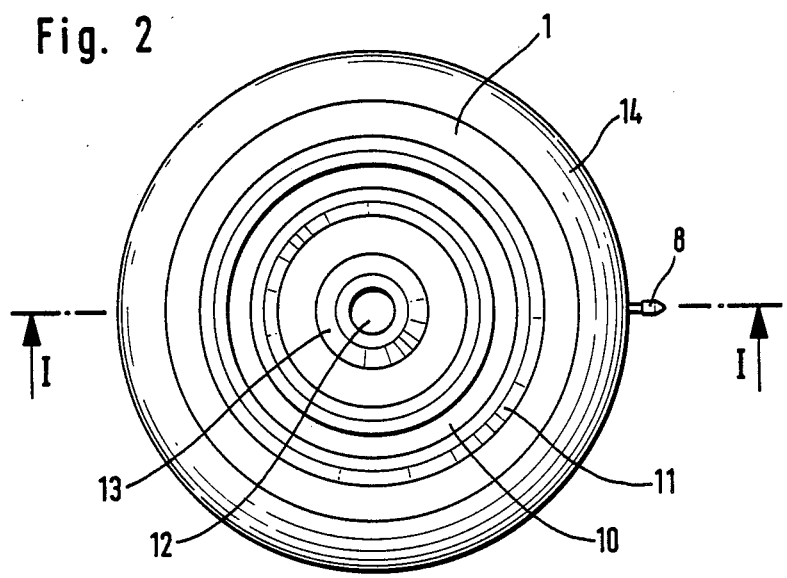
FIG. 2 shows a plan view of the device according to the invention according to claim 1.

As apparent from FIG. 2, the chamber 9 and thus the sealing ring 10 is disposed concentrically about the replenishing opening 12.

Via the outlet catheter 8 the implanted device continuously dispense the medicament disposed in the chamber 4 to the body of the patient. If now for medical reasons more of said medicament or an additional other medicament is to be introduced into the body of the patient then by means of an injection syringe at the piercing location shown by the positioned template the ring 10 is pierced and the medicament to be dispensed injected into the chamber 9 from which it is dispensed to the body directly via the outlet catheter 8. The flow resistance in the outlet reducing means 7 is so large that forcing back of the medicament into the chamber 4 of the implantable device is prevented. This need not necessarily be the same medicament or drug which is dispensed via the chamber 4 but for example for freeing the catheter 8 may also be heparin or a similar substance.

Figure 3:
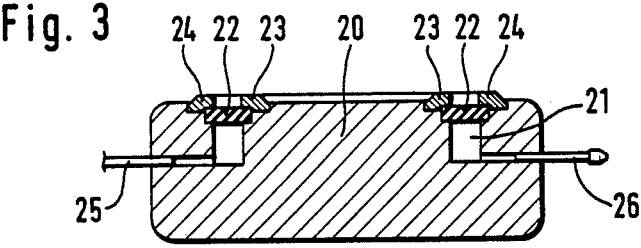
FIG. 3 shows a vertical section through an injection means for a medicament provided with the septum according to the invention.

In the example of embodiment according to FIG. 3 in a housing 20 an annular chamber 21 is provided which is open upwardly, i.e. in the direction towards the end face of the housing 20. The chamber 21 is sealed there by means of an annular septum 22 which is fixed by means of annular clamping members 23, 24 in the housing 20. 25 denotes the supply conduit for a long-term medicament and 26 the dispensing catheter.

Figure 4:
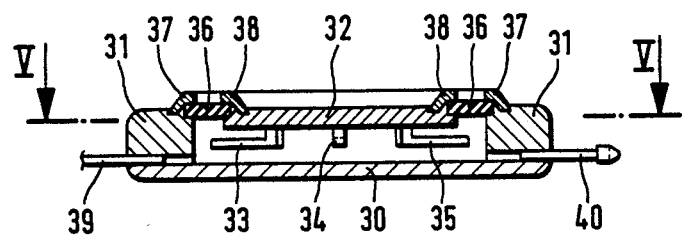
FIG. 4 shows a section along the line IV—IV of FIG. 5 of another embodiment of an injection means also provided with the septum according to the invention.

In the embodiment according to FIG. 4 a disc-shaped housing is likewise provided which consists of two parts, i.e. the bottom 30 and an upper part 31. In said upper part 31 a circular opening is provided in which a center piece 32 is centrally inserted and is secured via arms 33, 34, 35 on the upper part. Between the upper part 31 and the center piece 32 an annular space is left which is sealed via a likewise annular septum 36. The annular septum 36 is again secured with annular clamping members 37, 38 to the upper part or center piece. The center piece 32 has a smaller thickness than the height of the upper part 31 so that in the interior of the housing a chamber is left free in which the injected medicament is disposed. 39 denotes the supply conduit and 40 the outlet catheter. The form of the chamber is not critical and can be chosen in accordance with the intended purpose.

Figure 5:
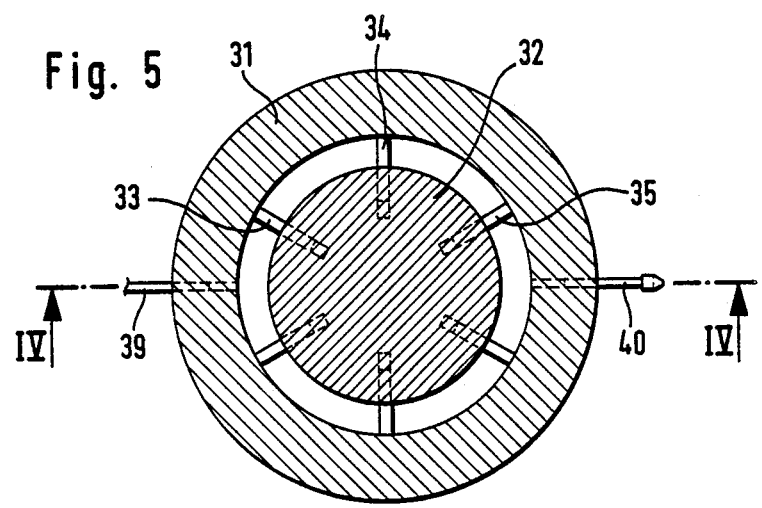
FIG. 5 shows a section along the line V—V of FIG. 4.

The embodiments according to FIGS. 3 to 5 are mere injection points for medicament whereas the embodiment according to FIGS. 1 and 2 is a device for dosed long-term administration of medicaments, which additionally comprises a means for injection of medicaments. All the embodiments have in common that the septum or one of the septa is annular, thereby achieving the advantages explained above.

In the modification of the embodiments illustrated in FIGS. 3 to 5 and employable as attachment to an infusion pump; the construction according to the invention can also serve as mere injection point for medicaments which are to be brought to specific organs, the respective hollow organ, for example the supplying vein, being inaccessible or very difficultly accessible. In this case the supply lines 25 and 39 are dispensed with so that only the outlet catheter 26 or 40 leads away from the implanted means.

We claim:

1. An implantable device for dispensing an active substance to a patient, said device comprising:
    a housing defining a medicament chamber;
    a wall of said housing defining an annular opening communicating with said medicament chamber;
    an annular first septum covering said annular opening; and
    means for sealingly engaging said septum to said housing.

2. The implantable device of claim 1, wherein said device further comprises:
    a flexible membrane separating said medicament chamber from a propellant chamber; and
    a propellant chamber for containing a propellant capable of expanding isobarically with evaporation, said propellant chamber cooperating with said medicament chamber through said flexible membrane to reduce the volume of said medicament chamber upon expansion of said propellant;
    said medicament chamber including a dispensing opening in fluid communication with a dispensing catheter.

3. The implantable device of claim 2, wherein said device further comprises:
    a replenishing opening in said housing in fluid communication with said medicament chamber; and means mounted to said replenishing opening for introducing a medicament to said medicament chamber; and a second septum sealing said replenishing opening.

4. The implantable device of claim 3, wherein:

said replenishing opening is disposed centrally on the medicament chamber housing; and said first septum is disposed concentrically with respect to said replenishing opening.

* * * * *